United States Patent [19]

Parker, III et al.

[11] Patent Number: 4,754,655
[45] Date of Patent: Jul. 5, 1988

[54] APPARATUS AND METHOD FOR SAMPLING HAZARDOUS MATERIAL

[76] Inventors: Frank M. Parker, III, 31535 Nichols Sawmill Rd.; David A. Lucas, 300 Lazy La., both of Magnolia, Tex. 77355

[21] Appl. No.: 26,059

[22] Filed: Mar. 16, 1987

[51] Int. Cl.⁴ .............................................. G01N 1/08
[52] U.S. Cl. ................................ 73/864.44; 73/864.51; 73/863.23
[58] Field of Search ........... 73/864.44, 864.45, 863.23, 73/864.41, 864.42, 864.43, 863.24, 863.25, 864.34, 864.35, 864.51, 864.74, 864.63

[56] References Cited

U.S. PATENT DOCUMENTS

| | | | |
|---|---|---|---|
| 1,416,354 | 5/1922 | Johnson | 73/864.51 |
| 2,167,393 | 7/1939 | Muncy | 73/864.44 X |
| 2,666,330 | 1/1954 | McAndrew | 73/864.44 |
| 3,074,162 | 1/1963 | Lentini | 73/864.44 X |
| 3,225,602 | 12/1965 | Barton | 73/864.45 X |
| 3,383,839 | 5/1968 | Hintermaier | 73/28 X |
| 4,437,333 | 3/1984 | Hands | 73/863.23 X |
| 4,498,547 | 2/1985 | Herkness | 73/864.44 X |
| 4,616,515 | 10/1986 | Dancoine | 73/863.23 X |

Primary Examiner—Tom Noland
Attorney, Agent, or Firm—Kenneth A. Roddy

[57] ABSTRACT

A sampling nozzle is operatively coupled to a vacuum device and has a tubular coring member removably mounted at its upper end for extracting a sample of material from goods suspected of being hazardous. A canister is removably carried in the nozzle beneath the coring member in co-active, in-feed relation therewith for receiving the extracted sample. Air passages through the nozzle sidewall cooperate with a conical shroud carried on the upper end of the nozzle to create a blanket of air vacuum surrounding the coring member and the area around which the sample has been extracted. A high efficiency particulate filter may also be provided between the nozzle and the vacuum device. The sample is extracted while the surrounding blanket of air vacuum is active by placing the sampling nozzle against the goods to be sampled with the coring member in firm contact with the surface of the goods and pressing the nozzle causing the coring member to penetrate the material. The blanket of air vacuum surrounding the coring member draws airborne particulate material, vapors, and fumes in the vicinity of the extracted sample into the nozzle to be filtered. The cored sample falls through the coring member into the canister. The coring member is removed from the nozzle, and a compression spring ejects the container partially outward of the nozzle and it is capped under the same vacuum blanket to sealingly contain the extracted sample after which it may be safely transported to a convenient location for further analysis.

29 Claims, 2 Drawing Sheets

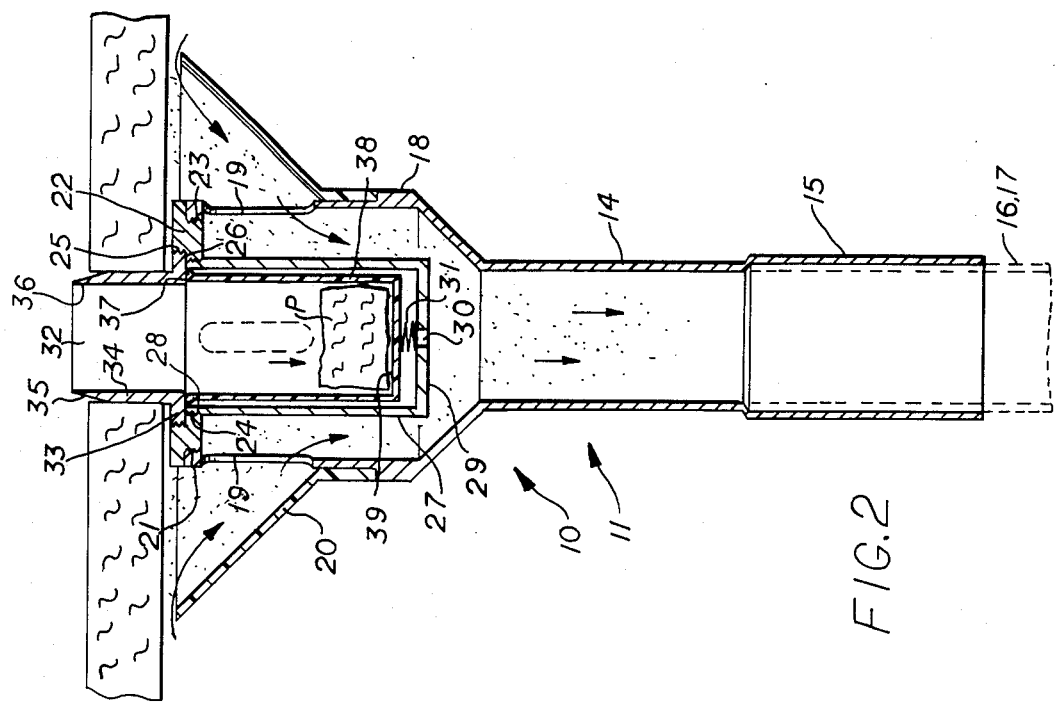
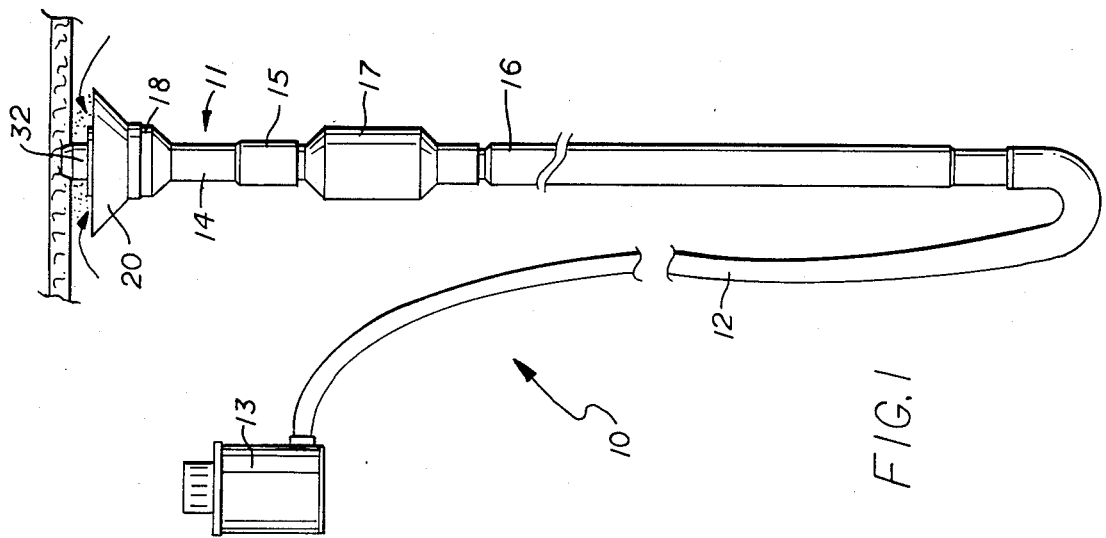

APPARATUS AND METHOD FOR SAMPLING HAZARDOUS MATERIAL

BACKGROUND OF THE INVENTION

1. Field of the Invention

This invention relates generally to methods and apparatus for sampling hazardous materials, and more particularly, to a method and apparatus for extraction and removal of cored samples of hazardous material and airborne particulates, vapors, and fumes which significantly reduces the release of hazardous materials to the atmosphere.

2. Brief Description of the Prior Art

Unprotected exposure to asbestos (including tremolite, anthophyllite and actinolite) is known to cause such fatal diseases as asbestosis, lung cancer, and mesothelioma. Construction materials containing these substances have been used extensively in schools, public buildings and private residences for over 50 years. The Federal Government as well as many state and local governments have set standards for allowable exposure to asbestos and testing for asbestos-containing materials (ACM) is required in schools and many public buildings.

Asbestos may be found in cement products, acoustical plaster, fireproofing textiles, wallboard, ceiling tiles, thermal insulation, floor tiles, roofing shingles and other materials widely used in the construction industry. Friable ACM has been grouped into three categories: (1) sprayed-on or troweled-on materials on ceilings, walls and other surfaces; (2) insulation on pipes, boilers, tanks, ducts, and other equipment; and (3) other miscellaneous products which are mostly nonfriable.

As awareness of the magnitude of asbestos content in building materials increased, a public demand for identification and evaluation through sampling followed. Accepted methods for removing samples of ACM for laboratory analysis involve the investigator removing the sample (often atop a ladder) with a knife or coring tool and placing the sample in a plastic bag. Since data available to date provide no evidence for the existence of a safe level of exposure, the prudent investigator must make every reasonable attempt to minimize, if not eliminate, exposure to the asbestos fibers. Therefore, for sample collection, a high efficiency respirator is worn by the investigator as well as disposable, protective clothing.

Because the prior art sampling techniques are substantially hazardous to unprotected building occupants, it is most often desirable to perform the sampling operation outside of normal hours of occupation. However, even with the greatest of care during sampling, asbestos exposure to the building occupants is probable since the disturbed fibers are carried throughout the building by air currents and remain in the system for extended periods of time.

The method and apparatus described herein provide a means by which samples of hazardous materials such as friable ACM can be removed safely under a high efficiency particulate air (HEPA) vacuum blanket. The airborne particulate material, vapors, and fumes are removed from the air by the invention and filtered from the air as the sample is taken and the sample container is sealed under the same vacuum blanket. The hazard of the materials to the investigator and building occupants is eliminated. The samples can be taken conveniently, during normal working hours without the use of special breathing devices or protective clothing.

There are several patents which disclose apparatus and methods for taking samples of various materials.

Johnson, U.S. Pat. No. 1,416,354 discloses a vacuum sampler for liquids comprising a cylindrical housing having an interior tube with an open bottom. The top of the housing is attached to a tubular member having a vent cock in the line. The device is lowered to the desired depth in a body of liquid and then the vent cock is opened causing the liquid to flow through the tube and into the housing.

Hintermaier, U.S. Pat. No. 3,383,839 discloses a vacuum device for collecting fibrous materials such a paper fibers. The patent is directed toward a clear plastic tubular member installed in a vacuum cleaner hose having one end attached to a vacuum cleaner. The other end of the hose is connected to a scraper/collector head. A wire mesh filter member is removably carried in the clear tubular member to capture fibers loosened by the scraping head.

McAndrew, U.S. Pat. No. 2,666,330 discloses a coring device for baled goods such as wool. The device comprises a cylindrical housing with a depending tubular coring tube having a removable cutting tip. A removable inverted can or receptacle is carried in the housing in communication with the coring tube and is retained in position by a resilient pad of sponge rubber on the floor of the housing. The coring tube is placed on a bale of wool and rotated to collect sample material in the receptacle.

Barton, U.S. Pat. No. 3,225,602 discloses a balance chamber for deep sea coring which is connected to a core barrel. The balance chamber has a lesser internal pressure than is exerted on the core barrel which has penetrated the ocean floor. The balance chamber can be suddenly opened to the core barrel by a valve creating a pressure imbalance which causes the movement of the sample material into the core barrel.

Herkness, U.S. Pat. No. 4,498,547 discloses an earth sampling tool comprising a sample bottle housing at the end of a rod which has a depending cone shaped probe. The removable sample bottle is inverted and compressibly retained in communication with the cone shaped probe by resilient material at the throat and bottom of the bottle. A sample is taken by pressing the probe into the soil.

The present invention is distinguished over the prior art in general, and these patents in particular by a sampling nozzle operatively coupled to a vacuum device and having a tubular coring member removably mounted at its upper end for extracting a sample of material suspected of being hazardous. A canister is removably carried in the nozzle beneath the coring member in co-active, in-feed relation therewith for receiving the extracted sample of material. Air passages through the nozzle sidewall cooperate with a conical shroud carried on the upper end of the nozzle to create a blanket of air vacuum surrounding the coring member and the area around which the sample will be extracted. A high efficiency particulate filter may also be provided between the nozzle and the vacuum device.

The sample is extracted while the surrounding blanket of air vacuum is active by placing the sampling nozzle against the goods to be sampled with the coring member in firm contact with the surface of the goods and pressing the nozzle to cause the coring member to penetrate the material. The blanket of air vacuum surrounding the coring member draws airborne particulate material, vapors, and fumes in the vicinity of the extracted sample into the nozzle to be filtered. The cored sample falls through the coring member into the canister. Under the surrounding vacuum blanket, the coring member is removed, and the canister is ejected partially outward of the nozzle and it is capped to sealingly contain the extracted sample of material afterwhich it may be safely transported to a convenient location for further analysis.

SUMMARY OF THE INVENTION

It is therefore an object of the present invention to provide a method and apparatus for removing and collecting samples of materials while trapping harmful material and fibers, vapors, and fumes.

It is another object of the invention to provide a method and apparatus for safely collecting debris, airborne particulates, vapors, and fumes in the vicinity of the sample, while removing a sample of the material.

It is another object of the invention to provide a method and apparatus for protecting the investigator/operator from exposure to harmful particles and fibers and providing a safe environment for bystanders during the sample taking.

It is another object of the invention to provide a method and apparatus whereby removal of samples may be carried out in a plurality of positions.

It is another object of the invention to provide a portable self cleaning sampling apparatus having a plurality of cutting tips and extension means for access to remote areas.

It is a further object of the invention to provide apparatus for collection of core samples for layer analysis and means for determining the thickness of material being sampled.

It is a still further object of the invention to provide apparatus which is simple in design, economical to manufacture, rugged and durable in use, and which may be used with conventional vacuum devices.

Other objects of the invention will become apparent from time to time throughout the specification and claims as hereinafter related.

The above noted objects and other objects of the invention are accomplished by a sampling nozzle operatively coupled to a vacuum device and having a tubular coring member removably mounted at its upper end for extracting a sample of material from the goods being sampled. A canister is removably carried in the nozzle beneath the coring member in co-active, in-feed relation therewith for receiving the extracted sample. A plurality of air passages through the nozzle sidewall cooperate with a conical shroud carried on the upper end of the nozzle to create a blanket of air vacuum surrounding the coring member and the area around which the sample will be extracted. A high efficiency particulate filter may also be provided between the nozzle and the vacuum device.

The sample is extracted while the surrounding blanket of air vacuum is created by placing the nozzle against the goods to be sampled with the coring member in firm contact with the surface of the goods and pressing the nozzle causing the coring member to penetrate the material. The blanket of air vacuum surrounding the coring member draws airborne particulate material, vapors, and fumes in the vicinity of the extracted sample into the nozzle to be filtered. The cored sample falls through the coring member into the canister. Under the vacuum blanket, the coring member is removed, and the canister is ejected partially outward of the nozzle and it is capped to sealingly contain the extracted sample afterwhich it may be safely transported to a convenient location for further analysis.

BRIEF DESCRIPTION OF THE DRAWINGS

FIG. 1 is a pictorial view in elevation of a preferred apparatus for taking samples of hazardous materials in accordance with the present invention.

FIG. 2 is a longitudinal cross section of the sampling nozzle of the present invention with a cutting tip installed.

DESCRIPTION OF THE PREFERRED EMBODIMENT

Figure 3:
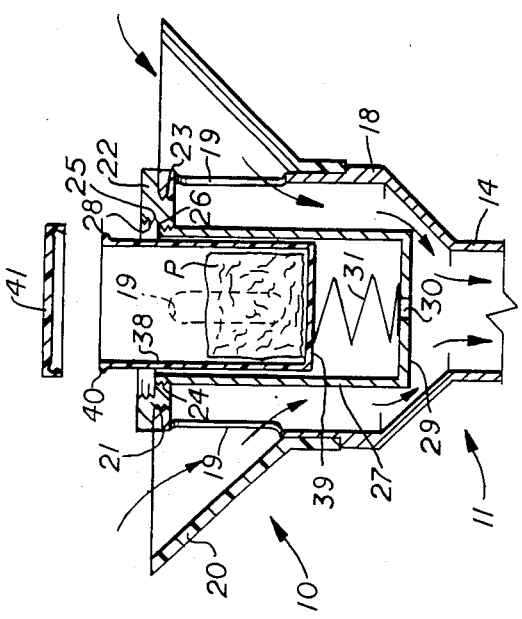
FIG. 3 is a longitudinal cross section of the sampling nozzle of the present invention illustrating the removal and sealing of the sample canister.

Referring to the drawings by numerals of reference, there is shown in FIGS. 1, 2, and 3, a preferred apparatus 10 for taking samples of hazardous materials. The apparatus comprises a sampling nozzle 11 attached to one end of a hose 12 which is connected at its other end to a vacuum device 13.

The sampling nozzle 11 comprises a tubular housing 14 the bottom end 15 of which is adapted to be slidably received on an extension tube 16 of the flexible hose 12. Optionally, as shown in FIG. 1, a suitable high efficiency particulate air filter device 17 may be installed between the nozzle 11 and the extension tube 16.

The upper end of the sampling nozzle 11 has an enlarged diameter 18 provided with a series of circumferentially spaced slots 19 and is surrounded by a funnel-shaped collector shield or conical shroud 20 extending outwardly therefrom. The angular sidewall of the funnel shaped shroud 20 converges to surround the enlarged diameter 18 at a point at, or just below, the lowermost portion of the slots 19. Threads 21 are provided at the top end of the enlarged diameter 18 just above the topmost portion of the slots 19.

A flat adapter ring 22 having a reduced diameter threaded portion 23 is threadedly received in the top end of the reduced portion 18. The adapter ring 22 has a threaded internal diameter 24 and a concentric larger threaded diameter 25 at its top end defining an annular shoulder 26 therebetween.

A tubular canister housing 27 having external threads 28 at its top end and an enclosed bottom 29 is threadedly received in the threaded internal diameter 24 of the adapter ring 22. An aperture 30 is provided in the bottom wall 29 which allows evacuation of materials which might otherwise be trapped in the housing. The sidewall of the canister housing 27 is spaced inwardly of the slots 19 to allow air flow therebetween. A compression spring 31 is disposed in the bottom 29 of the canister housing 27.

A coring member 32 having an externally threaded bottom flange 33, a tubular portion 34 extending upwardly therefrom, and a conical shaped cutting tip 35 at the top end is threadedly and removably received in the threaded diameter 25 of the adapted ring 22. The interior diameter 36 of the coring member 32 is smaller than the internal diameter of the canister housing 27 and when assembled in the adapter ring, the bottom of the flange 33 defines an annular shoulder 37 at the top of the canister housing 27.

It should be noted that the top surface of the adapter ring 22 extends above the top edge of the conical shroud 20, whereby when the cutter member 32 has penetrated the surface to be sampled, a small air space remains between the top edge of the shroud 20 and the surface of the sampled material.

A small canister 38 having an open top end and an enclosed bottom 39 is placed into the canister housing 27 on top of the spring 31, and the coring member is installed in the adapter ring 22 compressing the spring. The top end of the canister 38 is pressed upwardly against shoulder 37 formed by the bottom of the cutter member flange 33. As best shown in FIG. 3, a preferred canister 38 is formed of plastic, and has an annular bead 40 around the top end and will receive a resilient snap-fit cap 41 after the sample has been taken (explained hereinafter).

Figure 4:
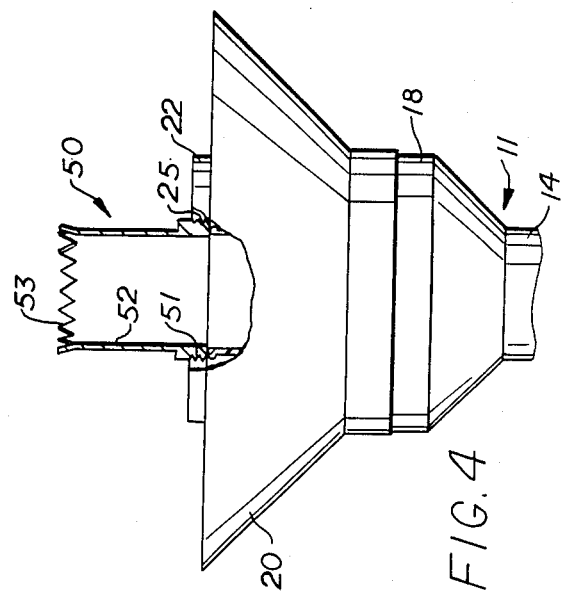
FIG. 4 is an elevational view in partial cross section of an alternate cutting tip to be used with the sampling nozzle.

FIG. 4 shows an alternate coring member 50 having an externally threaded bottom flange 51, a tubular portion 52 extending upwardly therefrom, and a toothed cutting edge 53 at the top end. The cutter member 50 is threadedly and removably received in the threaded diameter 25 of the adapted ring 22. As previously described in reference to cutter member 32, the interior diameter of the coring member is smaller than the internal diameter of the canister housing and when assembled in the adapter ring 22, the bottom of the flange 51 defines an annular shoulder at the top of the canister housing.

Figure 5:
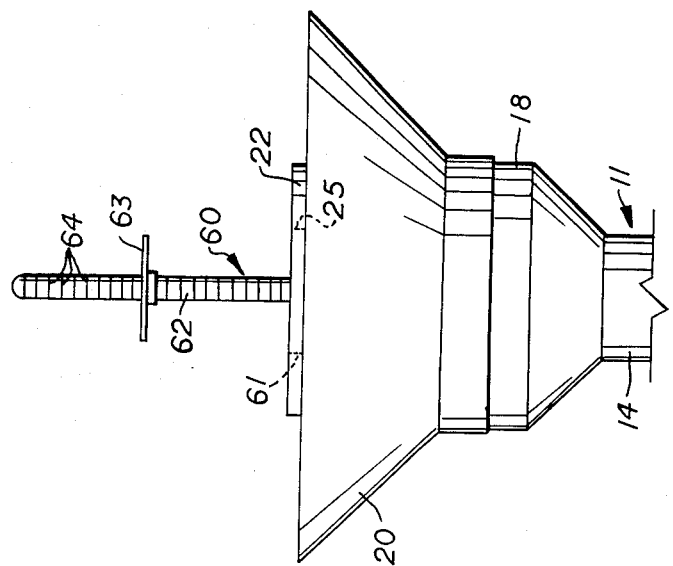
FIG. 5 is an elevational view of the sampling nozzle having a probe tip installed.

FIG. 5 shows a probe attachment 60 which may be installed in the adapter ring 22 in place of a cutter member. The probe attachment 60 comprises an externally threaded bottom flange 61, an elongate flat blade or a rod-like member 62 extending upwardly therefrom, and a laterally extending index member 63 slidably carried thereon. The rod-like portion 62 is divided along its length into equal increments with indicia 64 indicating measurements of predetermined scale. The probe 60 is threadedly and removably received in the threaded diameter 25 of the adapted ring 22. With the index member 63 at the top end of the rod-like member 62, the probe may be pushed into the material to be sampled and when removed, the index member will indicate the depth of penetration or the thickness of the goods sampled.

OPERATION

In use, the sampling nozzle 11 is placed on the extension tube 16 of the vacuum hose 12 or on the filter member installed thereon, and the vacuum device 13 is turned on. The coring member 32 is placed against material to be sampled, such as a friable or fibrous panel, and the nozzle is pressed upward to penetrate or cut a hole in the panel. The sample plug P of the hazardous material falls into the canister 38. Any fibrous debris, particulate material, vapors, or fumes in the air is pulled through the air space between the panel surface and the top edge of the conical shroud 20 and through the slots 19 to be captured in the filter 17 or in the filter inside the vacuum device 13.

With the vacuum blanket still active, the coring member 32 is removed and the canister 38 now containing the sample plug P is urged upward by the spring 31 and the cap 41 is snapped on the canister after which the sealingly contained sample may be safely transported to a convenient location for analysis.

It can be seen from the foregoing description, that the method and apparatus described therein provide a means by which samples of hazardous materials, such as friable ACM, can be removed safely under a high efficiency particulate air (HEPA) vacuum blanket. The airborne particulate material, vapors, and fumes are removed and filtered from the air as the sample is taken and the sample container is sealed under the same vacuum blanket. The hazard of the materials to the investigator and building occupants is reduced substantially. The samples can be taken conveniently, during normal working hours without the use of special breathing devices or protective clothing.

While this invention has been described fully and completely with special emphasis upon a preferred embodiment, it should be understood that within the scope of the appended claims the invention may be practiced otherwise than as specifically described herein.

We claim:

1. Apparatus for the extraction and containment of samples of materials suspected of being hazardous comprising
    a sampling nozzle having two ends and adapted to be operatively coupled at one end to air vacuum means and the other end adapted to penetrate, extract, and removably contain samples of goods suspected of being hazardous,
    said other end adapted to provide a blanket of air vacuum to surround the area around which the sample will be taken while simultaneously therewith drawing airborne materials, vapors, and fumes through the nozzle to be filtered.

2. Apparatus according to claim 1 in which
    the end of said sampling nozzle adapted to be operatively coupled to vacuum means is a lower end, and said apparatus further comprising;
    removable coring means at the upper end of said nozzle for extracting a sample of material from the goods being sampled,
    a sample container removably carried in said nozzle beneath said coring means in co-active in-feed relationship therewith for receiving an extracted sample of material,
    closure means for sealing said sample container, and
    means carried on the upper end of said nozzle for providing a blanket of air vacuum surrounding said coring means and the area around which the sample has been extracted for removing airborne particulate material, vapors, and fumes in the vicinity of the extracted sample.

3. Apparatus according to claim 2 in which
    said sampling nozzle comprises a tubular housing having a series of circumferentially spaced air passages through its sidewall beneath said coring means.

4. Apparatus according to claim 3 in which
    said air passages comprise a series of longitudinal elongated slots.

5. Apparatus according to claim 2 in which
    said sampling nozzle comprises a tubular housing having a series of circumferentially spaced air passages through its sidewall beneath said coring means, and
    said means for providing a blanket of air vacuum surrounding said coring means and the area around which the sample will be extracted comprises a concentric conical collector member on said housing extending outwardly and angularly upward therefrom to terminate at a predetermined distance beneath the upper end of said extraction means, said conical collector member sidewall converging at its lower end to surround the sidewall of said tubular housing in close proximity to the lowermost portion of said apertures, the uppermost end of said collector member spaced vertically relative to the upper portion of said coring means and said air passages to form a circumferential air passageway around said coring means and the area around which the sample will be extracted for drawing airborne particulate material, vapors, and fumes in the vicinity of the extracted sample into said collector member and through said apertures into said sampling nozzle.

6. Apparatus according to claim 2 in which
said coring means is removably mounted at the upper end of said nozzle.

7. Apparatus according to claim 2 in which
said coring means is threadedly received at the upper end of said nozzle.

8. Apparatus according to claim 2 in which
said coring means comprises a tubular cutter member removably mounted at the upper end of said nozzle and having a conical shaped cutting tip at the top end for penetrating the good to be sampled.

9. Apparatus according to claim 2 in which
said coring means comprises a tubular cutter member removably mounted at the upper end of said nozzle and having a toothed cutting edge at the top end for cutting the surface of the goods to be sampled upon rotation thereof and penetrating the goods to be sampled.

10. Apparatus according to claim 2 in which
said sample container comprises a tubular canister having a closed bottom end and an open top end disposed beneath said coring means and in communication therewith for receiving the extracted sample of material.

11. Apparatus according to claim 10 in which
said canister having an annular bead around its open top end, and
said closure member comprises a resilient snap-fit cap adapted to be removably received on said bead to seal the top end of said canister.

12. Apparatus according to claim 10 in which
said tubular canister is removably retained within a tubular canister housing having an enclosed bottom with an air passageway therethrough.

13. Apparatus according to claim 12 including
resilient means disposed between the bottom end of said canister and the bottom of said canister housing for retaining the open top end of said tubular canister in shock-resistive communication with said coring means when said coring means is installed on said sample nozzle, and
said resilient means ejecting said canister partially outward of said canister housing upon removal of said coring means from said nozzle.

14. Apparatus according to claim 12 in which
said resilient means comprises a compression spring.

15. Apparatus according to claim 2 including
a removable probe means at the upper end of said nozzle for determining the thickness of the goods to be sampled and the depth of penetration of said coring means when extracting a sample of material.

16. Apparatus according to claim 15 in which
said probe means comprises an elongate member divided along its length into equal increments representing measurements of predetermined scale.

17. Apparatus according to claim 15 in which
said probe means comprises an elongate rod-like member having an index member slidably carried thereon.

18. Apparatus according to claim 15 in which
said probe means comprises an elongate flat blade member having an index member slidably carried thereon.

19. Apparatus according to claim 1 including
vacuum means adapted to be operatively coupled to said nozzle for providing a source of vacuum thereto,
said vacuum means including high efficiency particulate filtering means.

20. Apparatus according to claim 19 in which
said vacuum means comprises an electrical vacuum device.

21. Apparatus according to claim 1 including
high efficiency particulate filtering means installed between said nozzle and a vacuum source.

22. A method of extracting and containing samples of material suspected of being hazardous which significantly reduces the release of possible hazardous materials to the atmosphere comprising the steps of;
providing a sampling nozzle having two ends and when in operation coupled at one end to air vacuum means and the other end adapted to penetrate, extract, and removably contain goods suspected of being hazardous while providing a blanket of air vacuum to surround the area around which the sample will be taken,
penetrating at least a portion of the goods to be sampled with said nozzle whereby a sample of the material of the goods penetrated will be extracted and removably contained within the nozzle, and
simultaneously therewith drawing airborne materials, vapors, and fumes through the nozzle by the surrounding blanket of air vacuum to be filtered.

23. The method according to claim 22 including the step of
providing particulate filtering means between said nozzle and said vacuum means.

24. The method according to claim 22 including the further steps of
removing the nozzle from the goods penetrated while drawing airborne materials, vapors, and fumes through the nozzle by the surrounding blanket of air vacuum, and
removing the extracted and removably contained sample from said nozzle under the surrounding blanket of air vacuum.

25. The method according to claim 24 including the step of
sealing the extracted sample within a container under the surrounding blanket of air vacuum.

26. The method according to claim 22
wherein said other end is a top end so that said two ends of said sampling nozzle are top and bottom ends and wherein said sampling nozzle is adapted to removably receive a tubular coring member at its top end and removably receive a sample container therebelow, the method further comprising the steps of providing air passage means for producing when in operation said blanket of air vacuum so as to surround the coring member and the area around which the sample will be extracted, installing said sample container in said nozzle, said sample container having an enclosed bottom end and an open top end, installing said coring member at the top end of said nozzle above said sample container in co-active in-feed relationship therewith for receiving an extracted sample of material, coupling said sampling nozzle bottom end to said air vacuum means, said air vacuum means having high efficiency particulate filtering means, and applying air vacuum to said nozzle, placing said sampling nozzle against the goods to be sampled with the coring member in firm contact with the surface of the goods and pressing said nozzle sufficiently to cause said coring member to penetrate the material of the goods, allowing a cored sample of the material to fall through said coring member into the container carried in said nozzle and thereafter removing said nozzle from the goods, simultaneously therewith providing the blanket of air vacuum so as to accomplish the surrounding of said coring member and the area around which the sample has been extracted to draw airborne particulate material, vapors, and fumes in the vicinity of the extracted sample into said nozzle to be filtered, and under the surrounding vacuum blanket, removing said coring member from said nozzle, removing said sample container from said nozzle and capping said container to sealingly contain the extracted sample of material whereby it may be safely transported to a convenient location for further analysis.

27. The method according to claim 26 including the step of installing said high efficiency particulate filtering member between said nozzle and said vacuum means prior to coupling said nozzle to said air vacuum means.

28. The method according to claim 26 including the step of pressing and rotating said nozzle after placing same against the goods to be sampled with the coring member in firm contact with the surface of the goods sufficiently to cause said coring member to cut through and penetrate the material of the goods.

29. The method according to claim 26 including the step of prior to installing said sample container and said coring member in said nozzle, installing an elongated probe member divided along its length into equal increments representing measurements of predetermined scale at the top end of said nozzle to extend upwardly therefrom, placing said sampling nozzle against the goods to be sampled with the probe member in firm contact with the surface of the goods and pressing said nozzle sufficiently to cause said probe member to penetrate the material of the goods, removing the probe from the goods and examining the increments to make a determination of the thickness of the goods to be sampled, removing the probe member from said nozzle, installing said sample container in said nozzle, and installing said coring member in said nozzle above said container, and thereafter continuing the steps recited for extracting the sample of material following installation of the coring member.

* * * * *